United States Patent
Kim et al.

(10) Patent No.: US 8,890,074 B2
(45) Date of Patent: Nov. 18, 2014

(54) APPARATUS AND METHOD FOR DETECTING DURABILITY WIPER BLADE

(75) Inventors: Hyun Sub Kim, Seoul (KR); Jun Mo Ku, Hwaseong-si (KR)

(73) Assignee: Hyundai Motor Company, Seoul (KR)

( * ) Notice: Subject to any disclaimer, the term of this patent is extended or adjusted under 35 U.S.C. 154(b) by 366 days.

(21) Appl. No.: 13/551,153

(22) Filed: Jul. 17, 2012

(65) Prior Publication Data

US 2013/0105694 A1     May 2, 2013

(30) Foreign Application Priority Data

Oct. 31, 2011    (KR) .................. 10-2011-0111799

(51) Int. Cl.
*G01J 5/02* (2006.01)
*B60S 1/08* (2006.01)
*G01N 21/55* (2014.01)
*B60S 1/38* (2006.01)

(52) U.S. Cl.
CPC ............... *B60S 1/0833* (2013.01); *G01N 21/55* (2013.01); *B60S 2001/3844* (2013.01)
USPC ..................................... 250/341.8

(58) Field of Classification Search
CPC ...................................... G01N 21/55
USPC ........................... 250/341.1–341.8
See application file for complete search history.

(56) References Cited

U.S. PATENT DOCUMENTS 5,319,293 A * 6/1994 Levers .......................... 318/483
6,057,660 A * 5/2000 Meier et al. .................. 318/483
6,157,024 A * 12/2000 Chapdelaine et al. ........ 250/221

FOREIGN PATENT DOCUMENTS

JP     2000-507902     6/2000

* cited by examiner

*Primary Examiner* — Kiho Kim
(74) *Attorney, Agent, or Firm* — Morgan, Lewis & Bockius LLP

(57) ABSTRACT

An apparatus for detecting durability of a wiper blade, may include an optical sensor including a light emitting unit radiating an infrared ray to a windshield glass and a light receiving unit receiving the infrared ray reflected through the windshield glass, wherein the wiper blade may be positioned between the light emitting unit and light receiving unit, and a controller comparing an infrared receiving quantity of the windshield glass transferred from the light receiving unit with a reference receiving quantity to determine an exchange time of the wiper blade.

8 Claims, 3 Drawing Sheets

US 8,890,074 B2

APPARATUS AND METHOD FOR DETECTING DURABILITY WIPER BLADE

CROSS-REFERENCE TO RELATED APPLICATIONS

The present application claims priority to Korean Patent Application No. 10-2011-0111799 filed on Oct. 31, 2011, the entire contents of which is incorporated herein for all purposes by this reference.

BACKGROUND OF THE INVENTION

1. Field of the Invention

The present invention relates to a technology of an apparatus and a method for detecting durability of a wiper blade so as to enable a driver to easily detect exchange time of the wiper blade.

2. Description of Related Art

As shown in FIG. 1, a windshield glass 1 of a vehicle is provided with a wiper 2 for securing a front sight of a driver by wiping rain, snow, foreign materials, or the like.

In connection with the wiper 2, when a driver operates a switch (multi function switch) to drive a wiper motor, one end of a wiper frame 2a rotates based on a center of the other end of the wiper frame 2a receiving power from the wiper motor and when the wiper frame 2a rotates, a wiper blade 2b made of a rubber material coupled with the wiper frame 2a wipes the windshield glass 1.

The wiper blade 2b is consumption goods and therefore, the wiping performance thereof is gradually degraded due to abrasion of rubber after the wiper blade 2b is used for predetermined time. The driver detects the exchange time of the wiper blade 2b through a stripe pattern generated on the windshield glass 1 when the wiper 2 is operated.

However, there may be a case in which the driver does not detect the exchange time of the wiper blade 2b through the stripe pattern generated on the windshield glass 1. In particular, a driver cannot see the stripe pattern well at the time of night driving and therefore, may miss the exchange time of the wiper blade 2b. In this case, accidents may occur due to a low front sight secure.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing an apparatus and a method for detecting durability of a wiper blade so as to enable a driver to easily see exchange time of the wiper blade by using infrared receiving quantity reflected through the windshield glass.

In an aspect of the present invention, an apparatus for detecting durability of a wiper blade, may include an optical sensor including a light emitting unit radiating an infrared ray to a windshield glass and a light receiving unit receiving the infrared ray reflected through the windshield glass, wherein the wiper blade is positioned between the light emitting unit and light receiving unit, and a controller comparing an infrared receiving quantity of the windshield glass transferred from the light receiving unit with a reference receiving quantity to determine an exchange time of the wiper blade.

A cluster alarm lamp may be lightened according to a control signal of the controller to inform a driver of the exchange time of the wiper blade.

A lens of the light emitting unit is a polyspheric lens for emitting the infrared ray at a plurality of angles to a plurality of light receiving units.

The windshield glass is provided with a plurality of prisms between the light emitting unit and the plurality of light receiving units for refracting the infrared ray radiated from the light emitting unit to the light receiving units.

In another aspect of the present invention, a method for detecting durability of a wiper blade, may include detecting an infrared receiving quantity of an optical sensor reflected through a windshield glass once per each one-time operation cycle of a wiper, to form one-time detected infrared receiving quantity, defining a state in which the one-time detected infrared receiving quantity is repeated predetermined times to be a unit period in which the receiving quantity is detected, and selecting a maximum receiving quantity per every the unit period in which the infrared receiving quantity is detected, and comparing the selected maximum receiving quantity with a reference receiving quantity, and determining that the wiper blade needs to be exchanged, when the maximum receiving quantity is determined to be the reference receiving quantity or less.

The one-time operation cycle is a cycle for the wiper to perform an operation of a falling state, a rising state, a re-falling state, and a returning state in which the wiper is returned to an original position.

The unit period in which the receiving quantity is detected is a period in which the one-time operation cycle is repeated five times to six times.

The method may further include informing a driver of the exchange time, when it is determined that the wiper blade needs to be exchanged.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
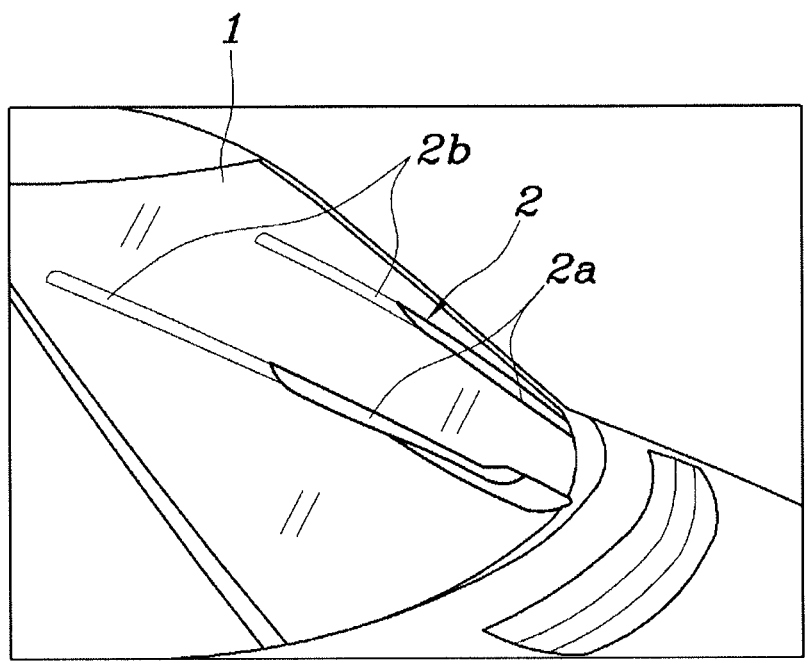
FIG. 1 is a diagram showing a wiper for a vehicle.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, an apparatus and a method for detecting durability of a wiper blade according to an exemplary embodiment of the present invention will be described with reference to the accompanying drawings.

Referring to FIG. 1, a windshield glass 1 of a vehicle is provided with a wiper 2 enabling a front sight secure of a driver. The wiper 2 may be configured to include a wiper frame 2a rotating by a wiper motor and a wiper blade 2b of a rubber material detachably coupled with the wiper frame 2a to wipe the windshield glass 1 when the wiper frame 2a rotates.

Figure 2:
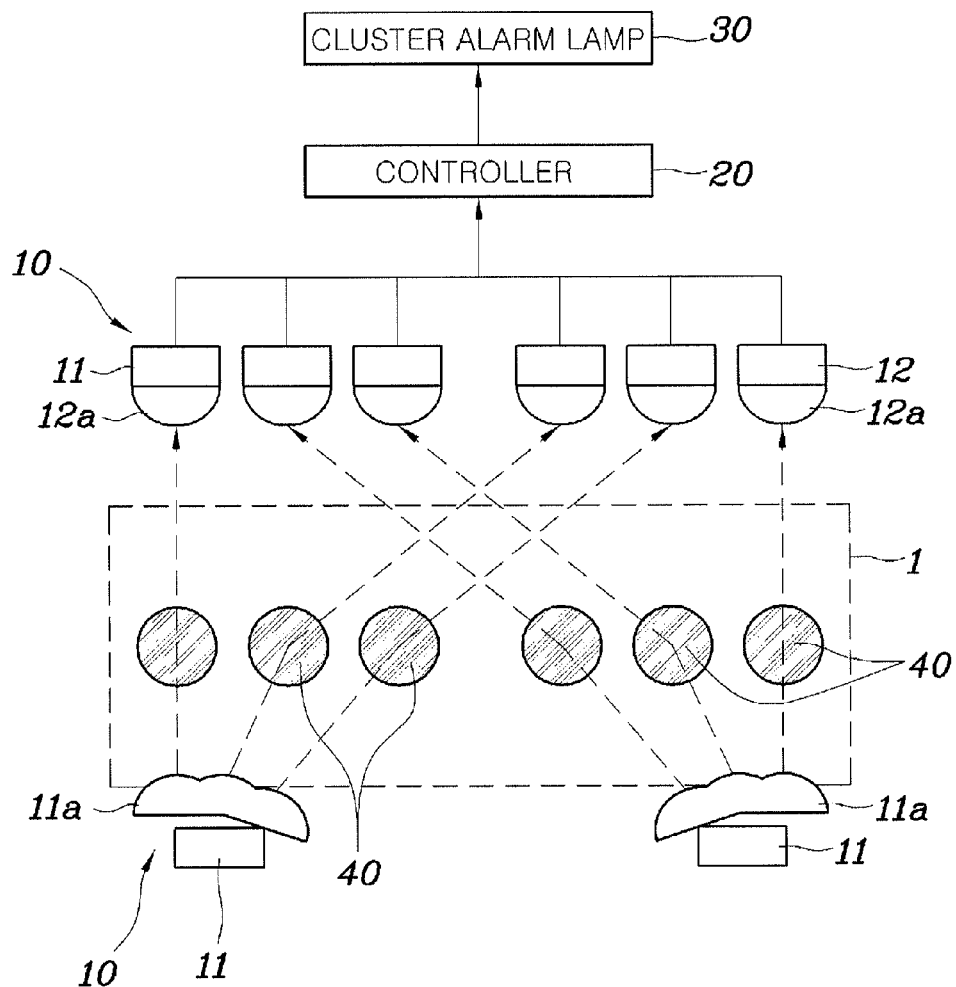
FIG. 2 is a diagram schematically showing a configuration of an apparatus for detecting durability of a wiper blade according to an exemplary embodiment of the present invention.

As shown in FIG. 2, an apparatus for detecting the wiper blade 2b according to an exemplary embodiment of the present invention may be configured to include an optical sensor 10 including a light emitting unit 11 radiating infrared rays to the windshield glass 1 and a plurality of light receiving unit 12 receiving infrared rays reflected through the windshield glass 1, a controller 20 having a function of comparing infrared receiving quantity of the windshield glass 1 transferred from the light receiving unit 12 with reference receiving quantity to detect the exchange time of the wiper blade, and a cluster alarm lamp 30 lightened according to a control signal of the controller 20 to inform a driver of the exchange time of the wiper blade 2b.

In this configuration, the number of light emitting units 11 is configured to be smaller than the light receiving unit 12, which results in reducing costs.

Since the number of light emitting units 11 is smaller than the number of light receiving units 12, the exemplary embodiment of the present invention can transfer infrared rays radiated from the light emitting unit 11 to the light receiving unit 12. To this end, a lens 11a of the light emitting unit 11 may be configured by a polyspheric lens for light-emitting infrared rays at various angles and the windshield glass 1 may be provided with a plurality of prisms 40 for refracting all the infrared rays radiated from the light emitting unit 11 to the light receiving unit 12.

Non-explained reference numeral 12a shown in FIG. 2 represents a lens of a light receiving unit, wherein the light receiving lens is a general single spheric surface lens.

Figure 3:
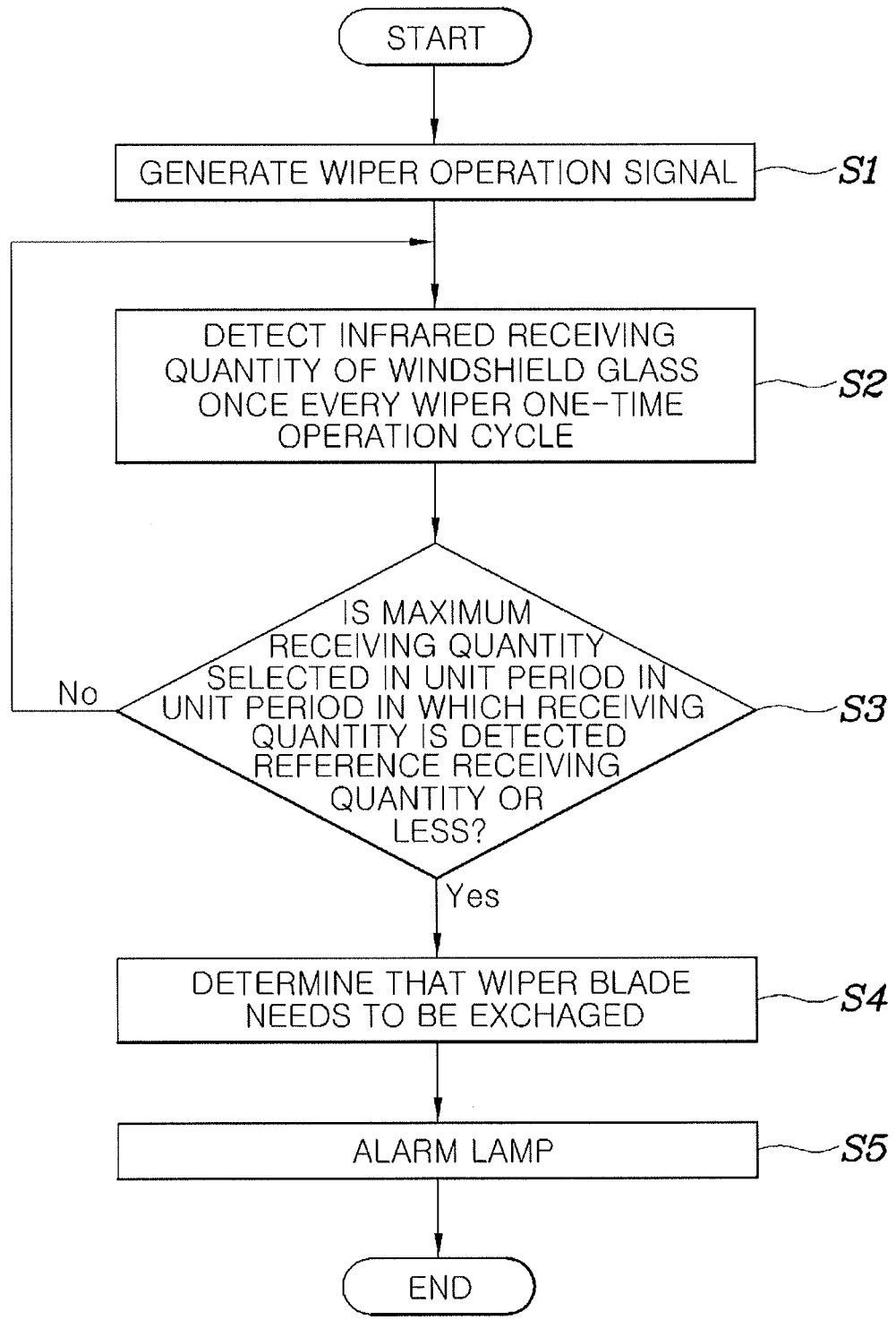
FIG. 3 is a flow chart for describing a method for detecting durability of a wiper blade according to the exemplary embodiment of the present invention.

Further, the method for detecting durability of a wiper blade according to the exemplary embodiment of the present invention will be described with reference to FIG. 3.

First, when the driver operates a multi function switch to generate an operation signal of the wiper 2 (S1), the wiper 2 is operated by receiving power from a wiper motor.

In an exemplary embodiment of the present invention, the light receiving unit 12 of the optical sensor 10 detects the infrared receiving quantity reflected through the windshield glass 1 once per each one-time operation cycle of the wiper and transfers the detected infrared receiving quantity to a controller 20 (S2).

In this case, the wiper one-time operation cycle is an operation of a falling state of the wiper 2, a rising state thereof, a re-falling state thereof, and a state in which the wiper is returned to an original position.

The controller 20 sets a state in which one-time detected infrared receiving quantity is repeated several times to be a unit period in which the receiving quantity is detected and selects only the maximum receiving quantity every the unit period in which the receiving quantity is detected and compares the selected maximum receiving quantity with the reference receiving quantity.

In this case, the unit period in which the receiving quantity is detected is a period in which the wiper one-time operation cycle is repeated five times to six times.

In this case, when the maximum receiving quantity selected in the unit period in which the receiving amount is detected is determined to be the reference receiving quantity or less (S3), the controller 20 determines that the wiper blade 2b needs to be exchanged (S4) and if it is determined that the wiper blade 2b needs to be exchanged, the controller 20 transmits the control signal to lighten the cluster alarm lamp 30 (S5). As a result, the driver sees the lighting state of the cluster alarm lamp 30 to easily detect the exchange time of the wiper blade 2b.

As described above, the apparatus and method for detecting durability of a wiper blade according to the exemplary embodiment of the present invention detects the exchange time of the wiper blade 2b by using the infrared receiving amount reflected through the windshield glass 1 and informs the driver of the information thereon, such that the driver can easily detect the exchange time of the wiper blade 2b.

Therefore, the driver can exchange the wiper blade 2b with the reduced durability at a proper time, such that he and she can secure the clear front sight at all times, thereby performing the safe driving.

As set forth above, the apparatus and method for detecting durability of a wiper blade according to the exemplary embodiment of the present invention can detect the durability of the wiper blade so as to enable the driver to easily see the exchange time of the wiper blade by using the infrared receiving quantity reflected through the windshield glass and inform the driver of the information thereon, thereby enabling the driver to easily detect the exchange time of the wiper blade.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An apparatus for detecting durability of a wiper blade, comprising:

an optical sensor including a light emitting unit radiating an infrared ray to a windshield glass and a light receiving unit receiving the infrared ray reflected through the windshield glass, wherein the wiper blade is positioned between the light emitting unit and light receiving unit; and a controller comparing an infrared receiving quantity of the windshield glass transferred from the light receiving unit with a reference receiving quantity to determine an exchange time of the wiper blade.

2. The apparatus of claim 1, further including a cluster alarm lamp lightened according to a control signal of the controller to inform a driver of the exchange time of the wiper blade.

3. The apparatus of claim 1, wherein a lens of the light emitting unit is a polyspheric lens for emitting the infrared ray at a plurality of angles to a plurality of light receiving units.

4. The apparatus of claim 3, wherein the windshield glass is provided with a plurality of prisms between the light emitting unit and the plurality of light receiving units for refracting the infrared ray radiated from the light emitting unit to the light receiving units.

5. A method for detecting durability of a wiper blade, including:

detecting an infrared receiving quantity of an optical sensor reflected through a windshield glass once per each one-time operation cycle of a wiper, to form one-time detected infrared receiving quantity;

defining a state in which the one-time detected infrared receiving quantity is repeated predetermined times to be a unit period in which the receiving quantity is detected, and selecting a maximum receiving quantity per every the unit period in which the infrared receiving quantity is detected, and comparing the selected maximum receiving quantity with a reference receiving quantity; and determining that the wiper blade needs to be exchanged, when the maximum receiving quantity is determined to be the reference receiving quantity or less.

6. The method of claim 5, wherein the one-time operation cycle is a cycle for the wiper to perform an operation of a falling state, a rising state, a re-falling state, and a returning state in which the wiper is returned to an original position.

7. The method of claim 5, wherein the unit period in which the receiving quantity is detected is a period in which the one-time operation cycle is repeated five times to six times.

8. The method of claim 5, further including informing a driver of the exchange time, when it is determined that the wiper blade needs to be exchanged.

* * * * *